United States Patent
Hu et al.

(10) Patent No.: US 10,713,264 B2
(45) Date of Patent: Jul. 14, 2020

(54) REDUCTION OF FEATURE SPACE FOR EXTRACTING EVENTS FROM MEDICAL DATA

(71) Applicant: International Business Machines Corporation, Armonk, NY (US)

(72) Inventors: Jianying Hu, Bronx, NY (US); Kun Lin, Bethesda, MD (US); Gigi Y. Yuen-Reed, Tampa, FL (US); Ping Zhang, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 342 days.

(21) Appl. No.: 15/246,899

(22) Filed: Aug. 25, 2016

(65) Prior Publication Data

US 2018/0060499 A1      Mar. 1, 2018

(51) Int. Cl.
| | |
|---|---|
| *G06F 16/2458* | (2019.01) |
| *G06N 5/02* | (2006.01) |
| *G06F 16/248* | (2019.01) |
| *G06F 16/28* | (2019.01) |
| *G06F 16/22* | (2019.01) |
| *G16H 40/67* | (2018.01) |
| *G16H 10/20* | (2018.01) |

(Continued)

(52) U.S. Cl.
CPC ...... *G06F 16/2477* (2019.01); *G06F 16/2228* (2019.01); *G06F 16/248* (2019.01); *G06F 16/285* (2019.01); *G06N 5/02* (2013.01); *G06N 20/00* (2019.01); *G16H 10/20* (2018.01); *G16H 10/60* (2018.01); *G16H 40/63* (2018.01); *G16H 40/67* (2018.01); *G16H 50/70* (2018.01)

(58) Field of Classification Search
CPC ............ G06F 19/324; G06F 17/30321; G06F 17/30551; G06F 17/30554; G06F 17/30598; G06F 19/00; G06F 16/2477; G06F 16/285; G06F 16/2228; G06F 16/248; G06N 5/02; G06N 20/00; G16H 40/67; G16H 50/70; G16H 40/63; G16H 10/20
USPC ........................................................ 705/2–3
See application file for complete search history.

(56) References Cited

U.S. PATENT DOCUMENTS

| | | | | |
|---|---|---|---|---|
| 5,742,811 | A | * | 4/1998 | Agrawal ................. G06F 16/30 |
| 6,092,065 | A | * | 7/2000 | Floratos ............... G06K 9/6218 |
| | | | | 707/737 |

(Continued)

OTHER PUBLICATIONS

Agrawal, Rakesh, "Fast algorithm for mining association rules", Proceedings of the 20th VLDB Conf., Santiago, Chile, p. 487-499 (Year: 1994).*

(Continued)

*Primary Examiner* — Jason S Tiedeman
*Assistant Examiner* — Rachel F Durnin
(74) *Attorney, Agent, or Firm* — Cantor Colburn LLP; Vazken Alexanian

(57) ABSTRACT

Embodiments include methods, systems and computer program products for reducing feature space in analysis of medical data. Aspects include receiving patient temporal traces. Aspects also include conducting sequential pattern mining on the patient temporal traces to produce sequential features. Aspects also include clustering the sequential features with a similarity metric. Aspects also include analyzing the clustered features to predict a healthcare outcome.

12 Claims, 8 Drawing Sheets

(51) Int. Cl.
*G16H 10/60* (2018.01)
*G06N 20/00* (2019.01)
*G16H 40/63* (2018.01)
*G16H 50/70* (2018.01)

(56) References Cited

U.S. PATENT DOCUMENTS

| | | | |
|---|---|---|---|
| 7,660,793 B2* | 2/2010 | Indeck | G06F 16/353 |
| | | | 707/999.005 |
| 8,280,640 B2 | 10/2012 | Levin et al. | |
| 8,706,519 B2 | 4/2014 | Gliklich | |
| 9,294,631 B1* | 3/2016 | Cogan | H04M 15/70 |
| 9,299,035 B2* | 3/2016 | Lakshmanan | G06N 20/00 |
| 9,633,097 B2* | 4/2017 | Tidwell | G06F 16/258 |
| 2004/0015337 A1 | 1/2004 | Thomas et al. | |
| 2005/0278324 A1* | 12/2005 | Fan | G06K 9/6215 |
| 2006/0155584 A1* | 7/2006 | Aggarwal | G06F 19/3418 |
| | | | 705/3 |
| 2009/0271433 A1* | 10/2009 | Perronnin | G06F 17/16 |
| 2010/0105989 A1* | 4/2010 | Inokuchi | G06F 19/325 |
| | | | 600/300 |
| 2012/0010867 A1 | 1/2012 | Eder | |
| 2012/0084101 A1 | 4/2012 | Qadri | |
| 2013/0196861 A1* | 8/2013 | Quake | G16B 30/00 |
| | | | 506/2 |
| 2014/0089003 A1* | 3/2014 | Frey | G06Q 10/06 |
| | | | 705/3 |
| 2014/0257847 A1* | 9/2014 | Hu | A61B 5/7282 |
| | | | 705/3 |
| 2014/0297323 A1* | 10/2014 | Hu | G06Q 50/24 |
| | | | 705/3 |
| 2014/0330843 A1* | 11/2014 | Park | G16B 40/00 |
| | | | 707/748 |
| 2015/0248470 A1* | 9/2015 | Coleman | A61B 5/0484 |
| | | | 707/740 |
| 2015/0324548 A1 | 11/2015 | Eder | |
| 2016/0026706 A1* | 1/2016 | Lum | G16H 50/70 |
| | | | 707/740 |
| 2017/0147753 A1* | 5/2017 | Han | G16H 50/50 |
| 2018/0166175 A1* | 6/2018 | Shah | G06F 19/326 |

OTHER PUBLICATIONS

Meila, Marina; Pentney, William, "Clustering by weighted cuts in directed graphs," University of Washington (Year: 2007).*

Ayres et al., "Sequential Pattern Mining Using a Bitmap Representation," Proceedings of the 8th ACM SIGKDD International Conference on Knowledge Discovery and Data Mining, 2002, pp. 429-435.

Batal et al., "A Temporal Pattern Mining Approach for Classifying Electronic Health Record Data," ACM Transactions on Intelligent Systems and Technology, vol. V., No. N, Article A, Publication date Aug. 2012, 20 pages.

Bechet et al., "Sequential Pattern Mining to Discover Relations Between Genes and Rare Diseases," Revue d'Intelligence Artificielle, vol. 28, No. 2-3, pp. 245-270, 2014.

Lin et al., "Improving Predictive Models With Clustered Sequences," IBM Research, Yorktown Heights, NY., 2002, 2 pages.

Pei, et al., "Mining Sequential Patterns Efficiently by Prefix-Projected Pattern Growth," Data Engineering, 2001 Proceedings., 17th Conference, pp. 215-224.

Perer et al., "Mining and Exploring Care Pathways from Electronic Medical Records with Visual Analytics," Journal of Biomedical Informatics, 2015; pp. 369-378.

Wang et al., "A Graph Based Methodology for Temporal Signature Identification from EHR," AMIA Annual Symposium Proceedings, 2015, pp. 1269-1278.

* cited by examiner

| Cluster A | Cluster B |
|---|---|
| 1,5,1,1,1,1,5,1,1,1,1,1 | 7,7,7,7,7,1 |
| 1,5,1,1,1,5,1,1,1,1,1,5,1,1,5,1,1,1,1,1 | 7,7,7,7,7,7,7,1 |
| 1,5,1,1,1,5,1,1,1,1,1 | 7,7,5,7,7,7 |
| 1,1,1,1,1,1,1,1,1 | 7,7,7,7,7,7,1,1 |
| 1,5,1,1,1,1,5,1,1,1,1,1,1,5,1,1,1,1,1,1,1,1 | 7,7,7,5,7 |
| 1,5,1,5,1,1,1,1,1,1,1 | 7,5,7,7,7 |
| 1,5,1,1,5,1,1,1,1,1 | 7,7,7,7,5 |
| 1,5,1,1,1,1,5,1,1,1,1,1,1,5,1,1,1,1,1,5,1,1,1,1,1,1,1,1 | 7,7,5,7,7 |
| 1,5,1,5,1,5,1,1,1,1,1 | 7,7,7,7,7,7,7,5,7 |
| 1,1,1,1,5,1,1,1,1,1 | 7,7,7,7,7,7,7,5,7,7,7 |
| 1,1,1,5,1,1,1,1,1 | 7,7,7,7,5,5 |
| 1,5,1,1,1,1,5,1,1,1,1,1,1,1,1,5,1,1,1,1,1,1|5,1,1,1,1,1,1,5,1,1,5,1,1,1,1,1 | 7,7,7,7,7,7,5,7,7 |
| 1,1,1,1,1,1,1,5,1,1,1,1,1 | 7,7,7,7,7,7,7,7,7,5,7,7 |
| 1,1|5,1,1,1,1,1,1,1,1,1,1 | 7,7,7,7,5,7,7,7 |
| 1,5,1,1,1,5,1,1,1,1,1,1,5,1,5,1,1,5,1,1,1,1 | |
| 5,5,1,1,1,1,1,1,1,1,1,1 | 7,7,7,7,5,7,7 |
| 1,5,1,1,5,1,1,1,5,1,1,1 | 7,7,7,7,7,7,7,5,7,7 |
| 1,1,1,1,5,1,1,1,1,1,1 | 7,7,7,7,7,7,7,7,7,5,7,7,7 |
| 1,5,1,1,1,1,5,1,1,5,1,1,1,1,1|5,1,1,1,1,5,1,1,1,1,1,1,1,1|5,1,1,5,1,1 | 7,7,7,7,7,7,5,7,7,7 |
| 1,5,1,1,1,5,5,1,1,1,1,1,1,1,1,1,1,1,1,1 | 7,7,7,7,7,7,7,5,7 |

FIG. 8

REDUCTION OF FEATURE SPACE FOR EXTRACTING EVENTS FROM MEDICAL DATA

BACKGROUND

The present invention relates generally to extracting interpretable sequential events from medical data, and more specifically to methods, systems and computer program products for reducing feature space in analysis of medical data.

The desire to connect past medical history with patient outcome demands analysis of increasingly large amounts of medical data input. As more patient medical record data is digitized and collected, not only is the data input increased, but the number of patterns mined from the data also increases. Pattern mining algorithms, which are used in the analysis of data to find correlating features, tend to produce a relatively large number of features, e.g., variables used to predict an output variable. For example, a predictive model could yield hundreds of thousands of features. Accordingly, as the number of patterns increases, so does the features space. Yet, large feature spaces, involving high volumes of data, are difficult to interpret and detrimentally impact computation speed. Because parsimonious models are preferable, reduction of feature space is highly desirable. However, reduction in feature space can result in a loss of predictive power of the analysis.

SUMMARY

In accordance with one or more embodiments, a computer-implemented method for predicting healthcare outcomes is provided. The method includes receiving, by a processor, a plurality of patient temporal traces. The method also includes conducting sequential pattern mining on the plurality of patient temporal traces to produce a plurality of sequential features. The method also includes clustering the sequential features with a similarity metric to create a plurality of clustered features. The method also includes analyzing the clustered features to predict a healthcare outcome.

In accordance with another embodiment, a computer program product for predicting healthcare outcomes is provided. The computer program product includes a computer readable storage medium having program instructions embodied therewith, the program instructions executable by a processor to cause the processor to receive a plurality of patient temporal traces. The instructions also cause the processor to conduct sequential pattern mining on the plurality of patient temporal traces to produce a plurality of sequential features. The instructions also cause the processor to cluster the sequential features with a similarity metric to create a plurality of clustered features. The instructions also cause the processor to analyze the clustered features to predict a healthcare outcome.

In accordance with a further embodiment, a processing system for predicting healthcare outcomes includes a processor in communication with one or more types of memory. The processor is configured to receive a plurality of patient temporal traces. The processor is also configured to conduct sequential pattern mining on the plurality of patient temporal traces to produce a plurality of sequential features. The processor is also configured to cluster the sequential features with a similarity metric to create a plurality of clustered features. The processor is also configured to analyze the clustered features to predict a healthcare outcome.

BRIEF DESCRIPTION OF THE DRAWINGS

The subject matter of the invention is particularly pointed out and distinctly claimed in the claims at the conclusion of the specification. The foregoing and other features and advantages of the one or more embodiments described herein are apparent from the following detailed description taken in conjunction with the accompanying drawings in which:

FIG. 8 illustrates exemplary clustered sequential features generated according to one or more embodiments.

DETAILED DESCRIPTION

Figure 1:
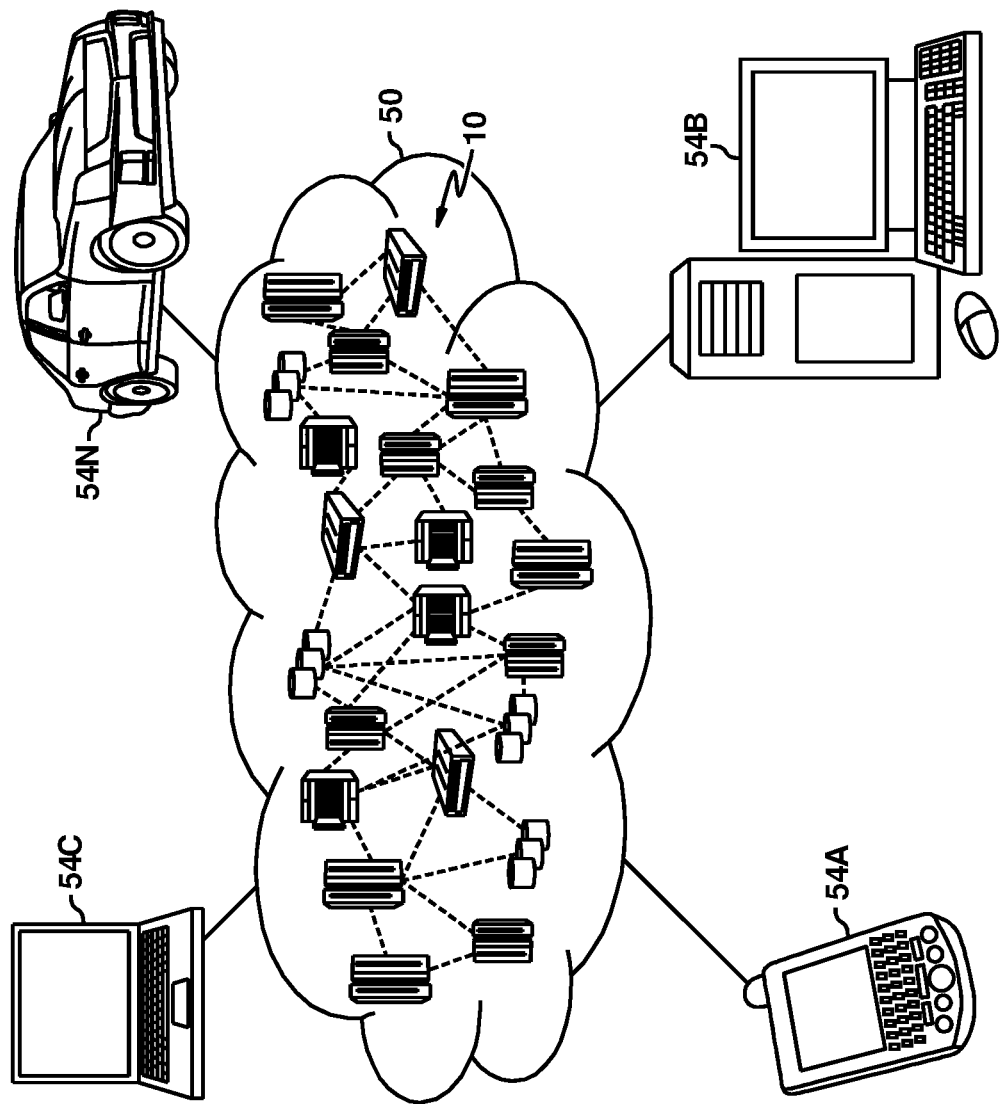
FIG. 1 depicts a cloud computing environment according to one or more embodiments of the present invention.

It is understood in advance that although this description includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
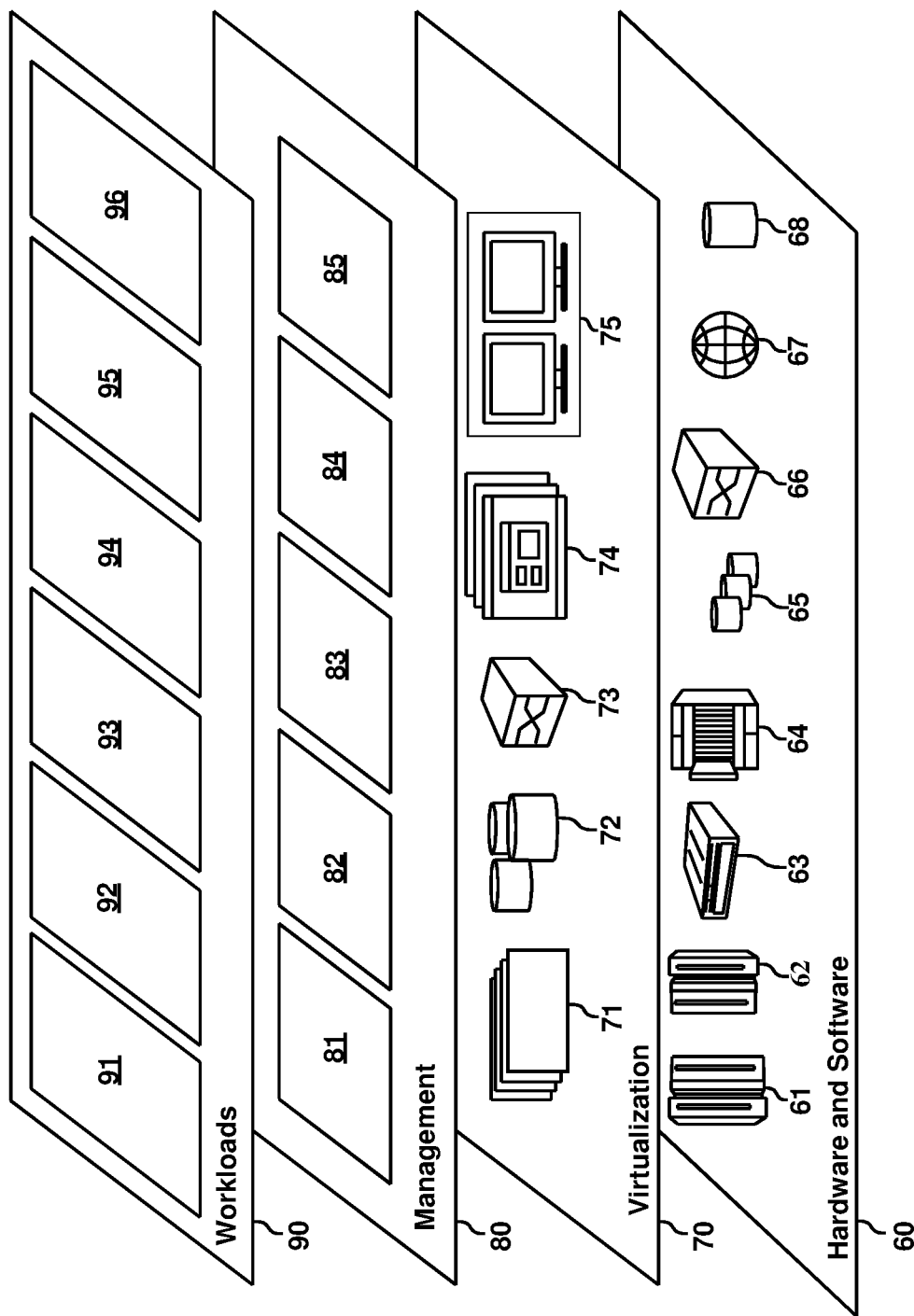
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and pattern mining 96.

Systems and methodologies for predicting healthcare outcomes are described herein. Medical records can contain a vast array of information that can be useful in predicting patient healthcare outcomes. For example, by comparing the incidence of a particular adverse event across a plurality of patient records, through data mining, features more likely to be associated with that event can be uncovered. However, as the available patient data and the number of potential associated features increase in magnitude, the analysis of patient data to predict healthcare outcomes becomes more complex and cumbersome. Embodiments described herein can reduce the feature space in the analysis of sequential patient data while maintaining or enhancing the predictive power of the pattern analysis. Embodiments described herein can also provide a feature reduction procedure that is intuitive and interpretable. Embodiments describe a method to extract interpretable sequential events from medical data to predict or understand a healthcare outcome.

Figure 3:
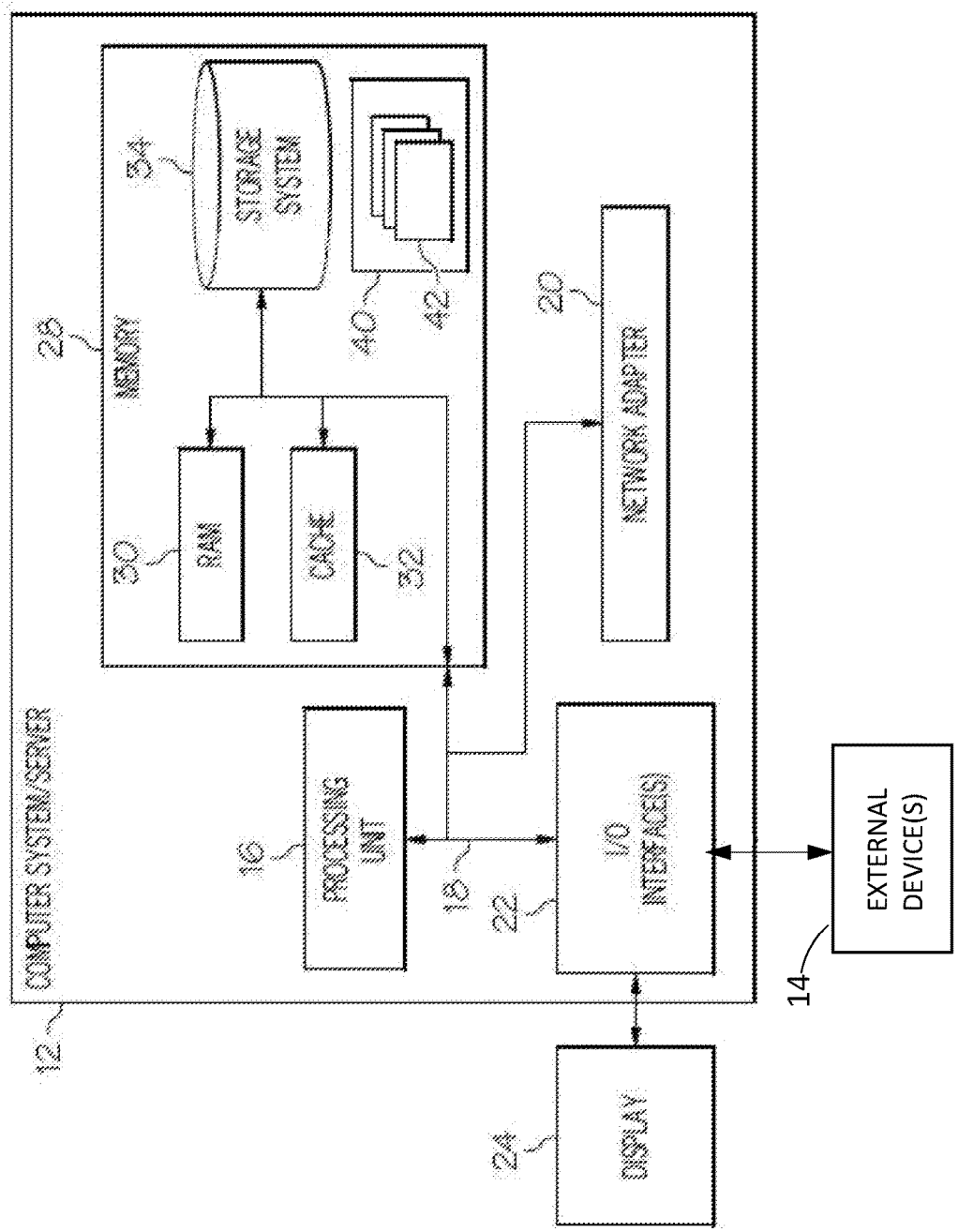
FIG. 3 is a computer system according to one or more embodiments.

Referring now to FIG. 3, a schematic of a cloud computing node 100 included in a distributed cloud environment or cloud service network is shown according to a non-limiting embodiment. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 4:
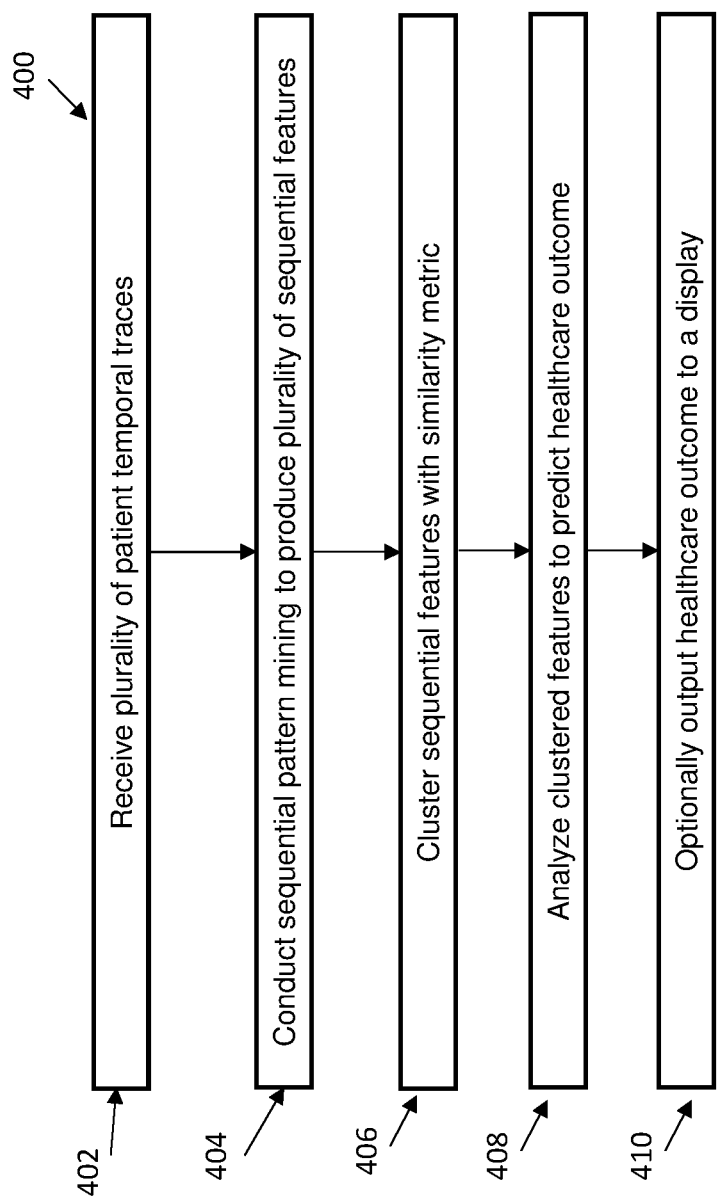
FIG. 4 is a flow diagram illustrating a method for predicting healthcare outcomes according to one or more embodiments.

Referring now to FIG. 4, a flow chart illustrating a method 400 for predicting a healthcare outcome is provided. The method 400 includes, as shown at block 402, receiving a plurality of patient temporal traces. The method 400 also includes, as shown at block 404, conducting sequential pattern mining to produce a plurality of sequential features. The method 400 also includes, as shown at block 406, clustering sequential features with a similarity metric. As shown at block 408, the method 400 also includes analyzing clustered features to predict a healthcare outcome. The method 400 optionally includes outputting the healthcare outcome to a display, as shown at block 410.

Patient temporal traces can include any data present in a patient medical record. In preferred embodiments, patient temporal traces can include a unique identifier, an ordered index, and an event. Patient temporal traces can be derived from databases, files, patient health records, such as longitudinal medical records, or other structured and unstructured data sources.

Unique identifiers can include various information included in the electronic health record (e.g., name, social security number, phone number, etc.) or by other means. In a specific implementation, a unique patient identifier is a globally unique identifier (GUID). The unique identifier can be any identifier associating an event with a patient, such as a patient ID number, medical record ID number, or the like.

In some embodiments, the ordered index provides a temporal or sequential identification, such as an indication of a date or time associated with an event. In some embodiments, the ordered index includes a time stamp.

The event can be any event useful in a predictive healthcare analysis. For example, the event can include a symptom, a reaction, or a treatment outcome. In some embodiments, the patient temporal traces contain features. Features can include any information related to a patient that might be useful in a predictive healthcare analysis. Such information includes, but is not limited to, demographic data, including age, gender, or ethnicity, current medical conditions, prior medical conditions, current symptoms, prior symptoms, height, weight, genomic data, current and prior medications, current and prior adverse events, treatment locations, treating physicians or medical providers, laboratory tests administered, and the like.

In some embodiments, the method includes conducting sequential pattern mining on the patient temporal traces to produce a plurality of sequential features. Any method of sequential pattern mining can be used in accordance with embodiments described herein. Sequential pattern mining can generate a large number of sequential patterns.

Figure 5:
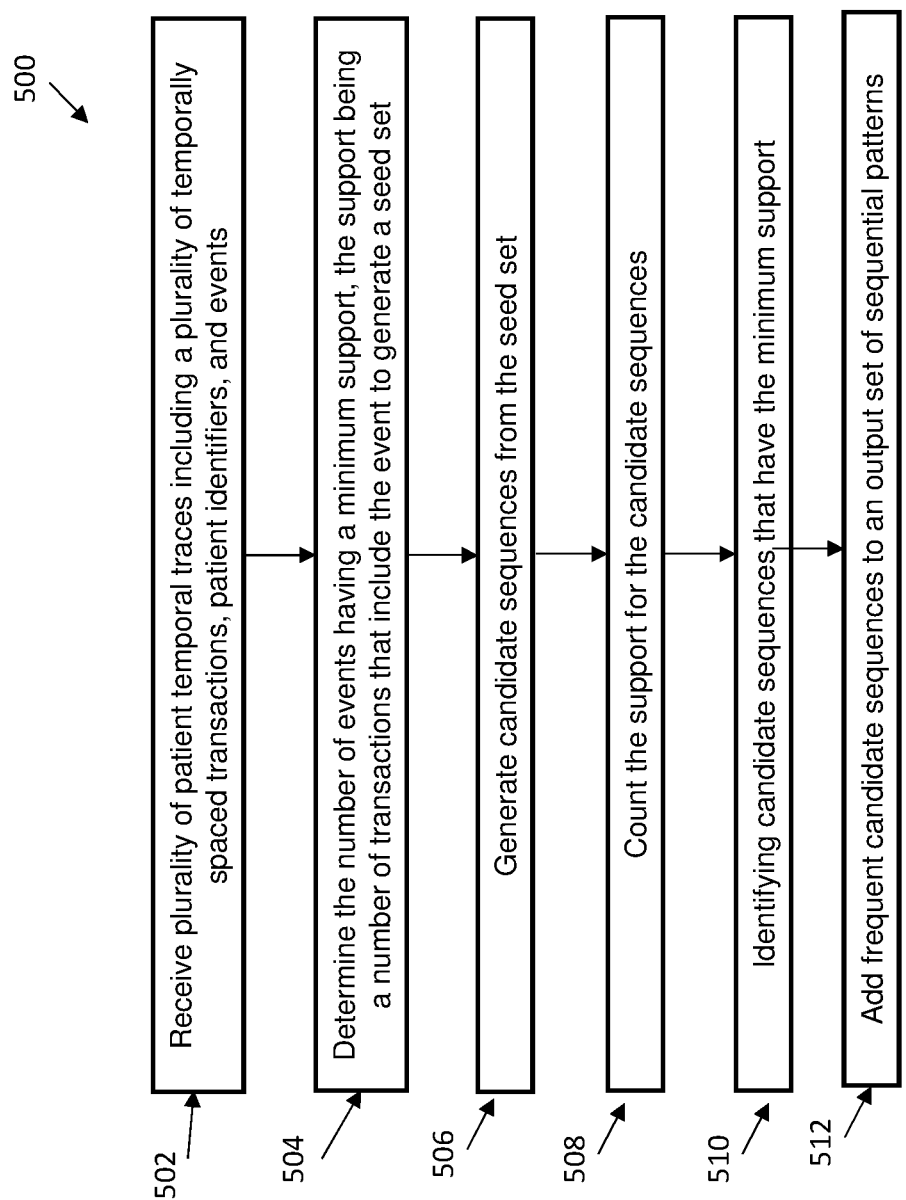
FIG. 5 is a flow diagram illustrating an exemplary method for conducting sequential pattern mining according to one or more embodiments.

FIG. 5 is a flow chart illustrating an exemplary method 500 for sequential pattern mining according to one or more embodiments. As is shown at block 502, the method 500 can include receiving a plurality of patient temporal traces including a plurality of temporally spaced transactions, patient identifiers, and events. The method 500 can also include, as shown at block 504, determining the number of events having a minimum support, the support being a number of transactions that include the event to generate a seed set. The method 500 can also include generating candidate sequences from the seed set, as shown at block 506. As shown at block 508, the method 500 can also include counting the support for the candidate sequences. As shown at block 510, the method 500 can include identifying candidate sequences that have the minimum support. As shown at block 512, the method 500 can include adding frequent candidate sequences to an output set of sequential patterns. In some embodiments, the output set of sequential patterns includes a set of frequent sequences and/or a plurality of sequential features.

Figure 6:
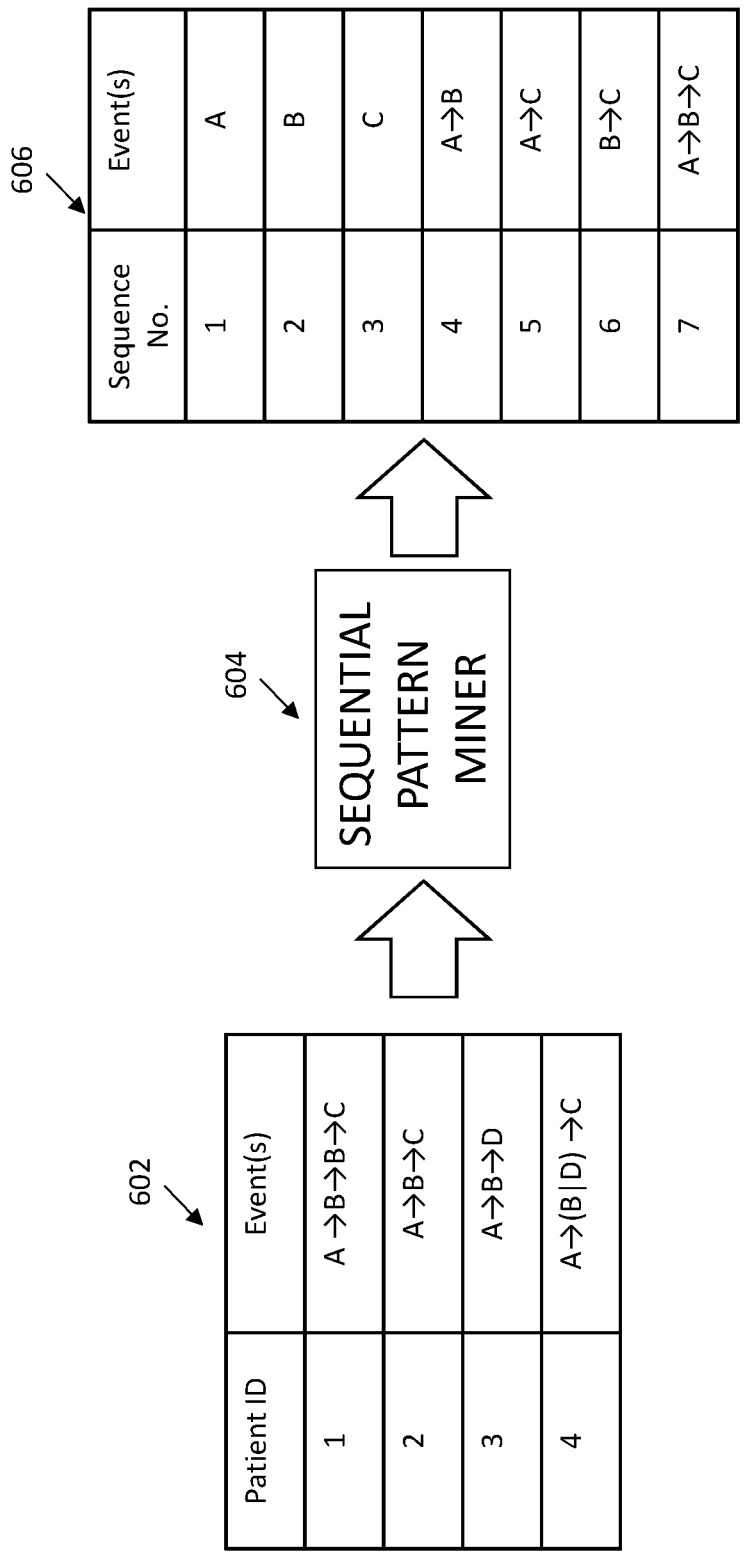
FIG. 6 is a diagram illustrating an exemplary output of sequential pattern mining according to one or more embodiments.

FIG. 6 illustrates an exemplary output of sequential pattern mining according to one or more embodiments. As is shown, an input 602 including a plurality of patient temporal traces can be provided. The input can include a patient ID and a number of temporally spaced transactions or events (designated A, B, C, and D). The input 602 can be provided to a sequential pattern miner 604, which can provide an output 606. The output 606 can include a series of candidate sequences including sequential features or events. The sequential pattern miner can also count the support for each candidate sequence (not shown).

In preferred embodiments, a method includes clustering sequential features with a similarity metric after conducting sequential pattern mining on the plurality of patient temporal traces. In some embodiments, clustering sequential features can reduce a total number of sequential pattern features. In some embodiments, clustering sequential features reduces the total number of sequential pattern features by greater than 50% relative to the number of sequential features produced prior to clustering. For example, clustering sequential features can reduce the total number of sequential features by greater than 75%, or greater than 90%, or greater than 95%.

Clustering the sequential features can include, in some embodiments, grouping a plurality of similar longitudinal sequential patterns together. In some embodiments, grouping the plurality of similar longitudinal sequential patterns together can include applying a symmetric nonnegative matrix factorization to the plurality of sequential features. According to one or more embodiments, any known clustering method based on a similarity metric can be used. Preferably, clustering the sequential features includes applying a Smith-Waterman based clustering algorithm, such as a Smith-Waterman Distance Matrix, to the plurality of sequential features. In some embodiments, clustering the sequential features includes nonnegative matrix factorization, such as Symmetric Nonnegative Matrix Factorization (SNMF). For example, SNMF can group similar longitudinal sequential patterns together.

Figure 7:
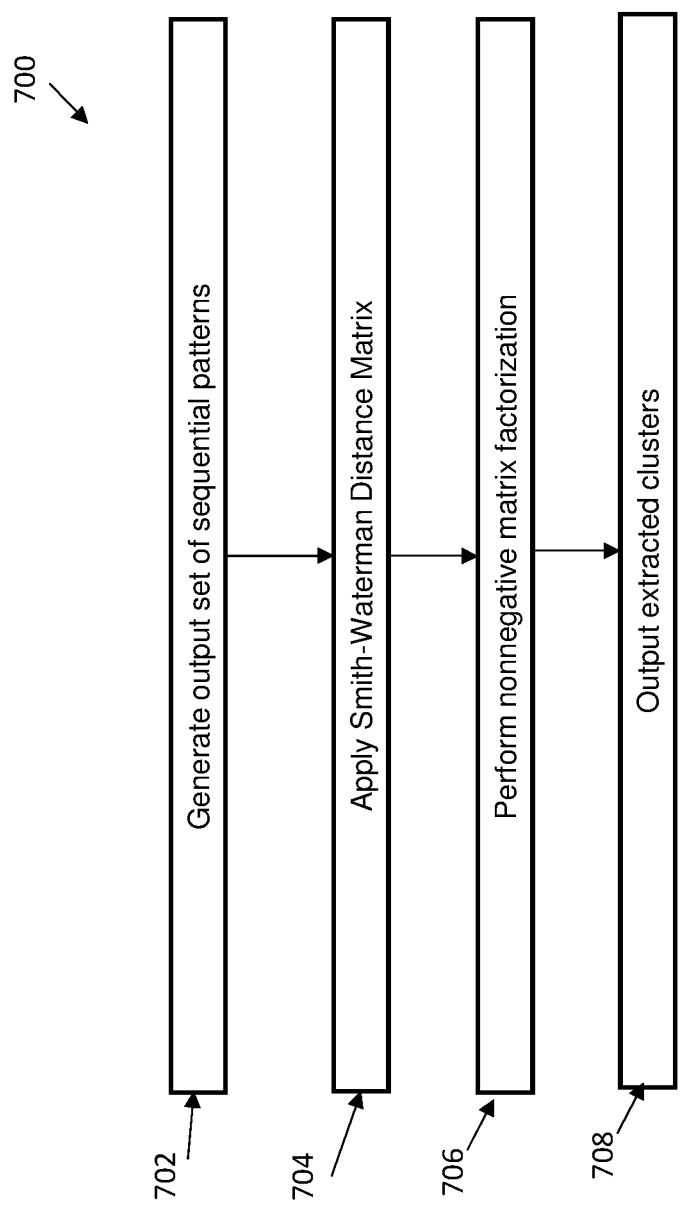
FIG. 7 is a flow diagram illustrating an exemplary method for clustering sequential features according to one or more embodiments.

FIG. 7 is a flowchart of an exemplary method 700 for clustering sequential features according to one or more embodiments. According to the method 700, an output set of sequential patterns is generated, as is shown in block 702. The exemplary method 700 then includes, as shown at block 704, applying a Smith-Waterman Distance Matrix to the output set of sequential patterns. The exemplary method 700 also includes performing nonnegative matrix factorization, as is shown at block 706. The method 700 also can include outputting extracted clusters, as is shown at block 708.

FIG. 8 illustrates a set of exemplary clustered sequence groups that can be produced in accordance with methods described herein. In accordance with the illustration, each row of the chart represents a sequential pattern in which 1 represents an exemplary drug combination of atorvastatin, fluvastatin, lovastatin, and pravastatin, 5 represents nystatin, and 7 represents simvastatin only. As is illustrated, separation by a comma indicates sequential administration, while separation by a vertical line indicates concurrent administration. Clustering sequential features can be used to generate two clusters, as shown. Cluster A, as can be seen, is a cluster representing predominantly the exemplary drug combination 1 or 1 with 5. Cluster B, as is shown, represents sequential patterns with predominantly simvastatin only. Complex patterns that cannot be represented by static features can thus become apparent after clustering.

An exemplary application of a Smith-Waterman algorithm is included below, in which Sequence 1=ACACACTA and Sequence 2=AGCACACA In accordance with the algorithm, H(i,j) is calculated as follows:

$$H(i, j) = \max \begin{cases} 0 \\ H(i-1, j-1) + s(a_i, b_j) & \text{Match/Mismatch} \\ \max_{k \geq 1} \{H(i-k, j) + W_k\} & \text{Deletion} \\ \max_{l \geq 1} \{H(i, j-1) + W_l\} & \text{Insertion} \end{cases},$$

$$1 \leq i \leq m, 1 \leq j \leq n$$

wherein similarity function S(a,b)=2 if a=b (reflecting a match) or −1 if a !=b (reflecting a mismatch), and with gap-scoring scheme W_i=−1, and wherein H and T are as follows:

$$H = \begin{pmatrix} & - & A & C & A & C & A & C & T & A \\ - & 0 & 0 & 0 & 0 & 0 & 0 & 0 & 0 & 0 \\ A & 0 & 2 & 1 & 2 & 1 & 2 & 1 & 1 & 2 \\ G & 0 & 1 & 1 & 1 & 1 & 1 & 1 & 0 & 1 \\ C & 0 & 1 & 3 & 2 & 3 & 2 & 3 & 2 & 2 \\ A & 0 & 2 & 2 & 5 & 4 & 5 & 4 & 4 & 4 \\ C & 0 & 1 & 4 & 4 & 7 & 6 & 7 & 6 & 6 \\ A & 0 & 2 & 3 & 6 & 6 & 9 & 8 & 8 & 8 \\ C & 0 & 1 & 4 & 5 & 8 & 8 & 11 & 10 & 10 \\ A & 0 & 2 & 3 & 6 & 7 & 10 & 10 & 10 & 12 \end{pmatrix}$$

$$T = \begin{pmatrix} & - & A & C & A & C & A & C & T & A \\ - & 0 & 0 & 0 & 0 & 0 & 0 & 0 & 0 & 0 \\ A & 0 & \nwarrow & \leftarrow & \nwarrow & \leftarrow & \nwarrow & \leftarrow & \leftarrow & \nwarrow \\ G & 0 & \uparrow & \nwarrow & \uparrow & \nwarrow & \uparrow & \nwarrow & \nwarrow & \uparrow \\ C & 0 & \uparrow & \nwarrow & \leftarrow & \nwarrow & \leftarrow & \nwarrow & \leftarrow & \leftarrow \\ A & 0 & \nwarrow & \uparrow & \nwarrow & \leftarrow & \nwarrow & \leftarrow & \leftarrow & \nwarrow \\ C & 0 & \uparrow & \nwarrow & \uparrow & \nwarrow & \leftarrow & \nwarrow & \leftarrow & \leftarrow \\ A & 0 & \nwarrow & \uparrow & \nwarrow & \uparrow & \nwarrow & \leftarrow & \leftarrow & \nwarrow \\ C & 0 & \uparrow & \nwarrow & \uparrow & \nwarrow & \uparrow & \nwarrow & \leftarrow & \leftarrow \\ A & 0 & \nwarrow & \uparrow & \nwarrow & \uparrow & \nwarrow & \uparrow & \nwarrow & \nwarrow \end{pmatrix}$$

In accordance with the exemplary exemplary application of a Smith-Waterman algorithm, an output is as follows:

Score=12

Sequence 1=A-CACACTA

Sequence 2=AGCACAC-A.

Clustered sequence groups can be used as features in a predictive model. Any known predictive model useful for predicting healthcare outcomes can be used. In preferred embodiments, the predictive model identifies a relationship between a sequence group and a healthcare outcome. In some embodiments, the predictive model provides a predicted healthcare outcome. For example, the predictive model can associate an event with a particular drug combination. In some embodiments, the predictive performance of the method is the same or improved relative to a method including data mining and applying a predictive model without clustering.

The methods described herein can include predicting a healthcare outcome. Predicting a healthcare outcome can include associating a sequence of events with a feature. For example, predicting a healthcare outcome can include determining that administration of a particular drug for a specified period of time is likely to result in complete recovery for a condition.

Thus, it can be seen from the forgoing detailed description that one or more embodiments of the present invention provide technical effects and benefits. Embodiments of the present invention provides reduced feature space in patient health data analysis, reducing computation time and reducing the complexity of the analysis.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting-data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for predicting healthcare outcomes, the method comprising:
    receiving, by a processor, a plurality of patient temporal traces, each of the temporal traces comprising a unique identifier, an ordered index, and a healthcare event;
    conducting, by the processor, sequential pattern mining on the plurality of patient temporal traces to produce a plurality of sequential features, by:
        determining, by the processor, a number of healthcare events having a minimum support, the minimum support comprising a number of transactions in the temporal traces that include the healthcare event;
        generating, by the processor, a seed set based on the number of healthcare events having the minimum support;
        generating, by the processor, candidate sequences based on the seed set;
        determining, for each of the candidate sequences, a frequency of the candidate sequence;
        selecting one or more of the candidate sequences based on the frequency of each respective candidate sequence; and
        generating, by the processor, the plurality of sequential features based on the one or more selected candidate sequences;
    clustering, by the processor, the sequential features with a similarity metric to create a plurality of clustered features, wherein clustering the sequential features comprises applying a Smith-Waterman Distance Matrix to the plurality of sequential features and performing nonnegative matrix factorization, wherein the sequential features comprise features of a feature space of a predictive model, wherein clustering the sequential features reduces a total number of sequential pattern features to reduce the feature space of the predictive model and create a reduced feature space of the predictive model, and wherein the plurality of clustered features comprise features of the reduced feature space of the predictive model; and
    analyzing, by the processor, the clustered features to predict a healthcare outcome, wherein predicting the healthcare outcome comprises applying the predictive model to the reduced feature space of the predictive model and outputting a predicted outcome to a display, wherein the predictive model identifies a relationship between a respective clustered feature of the reduced feature space and a respective healthcare outcome, and wherein the predicted healthcare outcome represents a likelihood that a specified drug treatment will result in recovery for a condition.

2. The computer-implemented method of claim 1, wherein the ordered index comprises a time stamp.

3. The computer-implemented method of claim 1, wherein clustering the sequential features comprises grouping a plurality of similar longitudinal sequential patterns together.

4. The computer-implemented method of claim 3, wherein grouping the plurality of similar longitudinal sequential patterns together comprises applying a symmetric nonnegative matrix factorization to the plurality of sequential features.

5. A computer program product for predicting healthcare outcomes, the computer program product comprising:

a non-transitory storage medium readable by a processing circuit and storing instructions for execution by the processing circuit for performing a method comprising:

receiving a plurality of patient temporal traces, each of the temporal traces comprising a unique identifier, an ordered index, and a healthcare event;

conducting sequential pattern mining on the plurality of patient temporal traces to produce a plurality of sequential features, by:

determining a number of healthcare events having a minimum support, the minimum support comprising a number of transactions in the temporal traces that include the healthcare event;

generating a seed set based on the number of healthcare events having the minimum support;

generating candidate sequences based on the seed set;

determining, for each of the candidate sequences, a frequency of the candidate sequence;

selecting one or more of the candidate sequences based on the frequency of each respective candidate sequence; and generating the plurality of sequential features based on the one or more selected candidate sequences;

clustering the sequential features with a similarity metric to create a plurality of clustered features, wherein clustering the sequential features comprises applying a Smith-Waterman Distance Matrix to the plurality of sequential features and performing nonnegative matrix factorization, wherein the sequential features comprise features of a feature space of a predictive model, wherein clustering the sequential features reduces a total number of sequential pattern features to reduce the feature space of the predictive model and create a reduced feature space of the predictive model, and wherein the plurality of clustered features comprise features of the reduced feature space of the predictive model; and analyzing the clustered features to predict a healthcare outcome, wherein predicting the healthcare outcome comprises applying the predictive model to the reduced feature space of the predictive model and outputting a predicted outcome to a display, wherein the predictive model identifies a relationship between a respective clustered feature of the reduced feature space and a respective healthcare outcome, and wherein the predicted healthcare outcome represents a likelihood that a specified drug treatment will result in recovery for a condition.

6. The computer program product of claim 5, wherein the ordered index comprises a time stamp.

7. The computer program product of claim 5, wherein clustering the sequential features comprises grouping a plurality of similar longitudinal sequential patterns together.

8. The computer program product of claim 7, wherein grouping the plurality of similar longitudinal sequential patterns together comprises applying a symmetric nonnegative matrix factorization to the plurality of sequential features.

9. A processing system for predicting healthcare outcomes, comprising:

a processor in communication with one or more types of memory, the processor configured to:

receive a plurality of patient temporal traces, each of the temporal traces comprising a unique identifier, an ordered index, and a healthcare event;

conduct sequential pattern mining on the plurality of patient temporal traces to produce a plurality of sequential features, by:

determining a number of healthcare events having a minimum support, the minimum support comprising a number of transactions in the temporal traces that include the healthcare event;

generating a seed set based on the number of healthcare events having the minimum support;

generating candidate sequences based on the seed set;

determining, for each of the candidate sequences, a frequency of the candidate sequence;

selecting one or more of the candidate sequences based on the frequency of each respective candidate sequence; and generating the plurality of sequential features based on the one or more candidate sequences;

cluster the sequential features with a similarity metric to create a plurality of clustered features, wherein clustering the sequential features comprises applying a Smith-Waterman Distance Matrix to the plurality of sequential features and performing nonnegative matrix factorization, wherein the sequential features comprise features of a feature space of a predictive model, wherein clustering the sequential features reduces a total number of sequential pattern features to reduce the feature space of the predictive model and create a reduced feature space of the predictive model, and wherein the plurality of clustered features comprise features of the reduced feature space of the predictive model; and analyze the clustered features to predict a healthcare outcome, wherein predicting the healthcare outcome comprises applying the predictive model to the reduced feature space of the predictive model and outputting a predicted outcome to a display, wherein the predictive model identifies a relationship between a respective clustered feature of the reduced feature space and a respective healthcare outcome, and wherein the predicted healthcare outcome represents a likelihood that a specified drug treatment will result in recovery for a condition.

10. The processing system of claim 9, wherein the ordered index comprises a time stamp.

11. The processing system of claim 9, wherein clustering the sequential features comprises grouping a plurality of similar longitudinal sequential patterns together.

12. The processing system of claim 11, wherein grouping the plurality of similar longitudinal sequential patterns together comprises applying a symmetric nonnegative matrix factorization to the plurality of sequential features.

* * * * *